United States Patent [19]

Childs et al.

[11] 4,331,024
[45] May 25, 1982

[54] OCTANE NUMBER MEASURING SYSTEM

[75] Inventors: W. Ves Childs; Herbert N. Coyner, both of Bartlesville, Okla.

[73] Assignee: Phillips Petroleum Company, Bartlesville, Okla.

[21] Appl. No.: 147,888

[22] Filed: May 8, 1980

[51] Int. Cl.³ ............................................. G01N 33/22
[52] U.S. Cl. ........................................................ 73/35
[58] Field of Search ............................................. 73/35

[56] References Cited

U.S. PATENT DOCUMENTS

| | | | |
|---|---|---|---|
| 2,936,609 | 5/1960 | Pope et al. | 73/35 |
| 3,183,708 | 5/1965 | Roddick | 73/35 |
| 3,318,136 | 5/1967 | Payne et al. | 73/35 |
| 3,469,954 | 9/1969 | Hoffman et al. | 44/2 |
| 3,503,722 | 3/1970 | Weber et al. | 73/35 X |
| 3,969,922 | 7/1976 | Baker et al. | 73/35 |
| 4,010,358 | 3/1977 | Morris | 73/35 X |

OTHER PUBLICATIONS

"Mercedes-Benz 280E", *Car and Driver Magazine*, pp. 62-68, 3/77.

*Primary Examiner*—James J. Gill

[57] ABSTRACT

First and second reference fuels having different known octane numbers and a test fuel having an unknown octane number are each provided individually through a pump to the fuel inlet of an engine at the substantially constant mass flow rate which results in substantially maximum knocking conditions for each of the fuels. The octane number of the test fuel is determined based on measurements of the rate of change of the cylinder pressure in the engine when the first and second reference fuels and the test fuel are flowing to the engine.

12 Claims, 4 Drawing Figures

OCTANE NUMBER MEASURING SYSTEM

This invention relates to method and apparatus for determining the octane number of a fuel. In one aspect this invention relates to method and apparatus for increasing the speed at which the octane number of a fuel can be determined and for reducing the quantity of fuel required to determine the octane number of the fuel.

There are many standard methods for determining the octane number of various fuels. Examples of these standard methods include ASTM Method D-2699-79 for the research octane number of gasoline and ASTM Method D-2700-79 for the motor octane number of gasoline. To determine the octane number of a test fuel in accordance with the ASTM methods, an ASTM-CFR engine is operated with the test fuel and with at least two reference fuels under conditions that will cause maximum knock. A pressure transducer is utilized to monitor the cylinder pressure and produce a voltage signal that is proportional to the rate of change in that pressure. A detonation meter is utilized to filter, integrate and amplify the output of the pressure transducer to produce a voltage signal that is proportional to the knock intensity. This signal is utilized to drive a knock meter which gives a scale reading relating to knock intensity. A comparison of the knock meter readings produced by the combustion of the reference fuels with the knock meter reading produced by the combustion of the test fuel is utilized to estimate the octane number of the test fuel.

The ASTM methods and most other standard methods require that the engine must be operated under maximum knocking conditions for each fuel being provided to the engine. In the ASTM method, the air/fuel ratio that results in maximum knock is found by a successive approximation method. In the ASTM method, the fuel level in a carburetor float bowl is moved up and down while the knock meter response is noted. This takes considerable time and fuel.

Many times in commercial operations the measurement of the octane number of a fuel must be accomplished quickly if optimum control over the process is to be based on the measured octane number. In the case of test fuels produced in a laboratory, many times there is only a very small quantity of the test fuel available for determining the octane number. It is thus desirable to be able to measure the octane number of a test fuel very quickly and with a small amount of the test fuel and it is an object of this invention to provide method and apparatus for increasing the speed at which the octane number of a test fuel is determined and for reducing the quantity of fuel required to determine the octane number of the test fuel.

In accordance with the present invention, method and apparatus are provided in which the fuel flow rate to the engine which gives maximum knock is set directly by providing both the reference fuels and the test fuel to the engine at the same substantially constant mass flow rate which results in maximum knock. The direct setting of the fuel flow rate to the flow rate which will produce maximum knock results in a substantial increase in the speed at which the octane number of a fuel can be determined and also substantially reduces the quantity of fuel required to determine the octane number of the fuel because the successive approximations of the ASTM methods and other standard methods are not required.

Other objects and advantages of the invention will be apparent from the foregoing brief description of the invention and from the claims as well as from the detailed description of the drawings in which:

Figure 1:
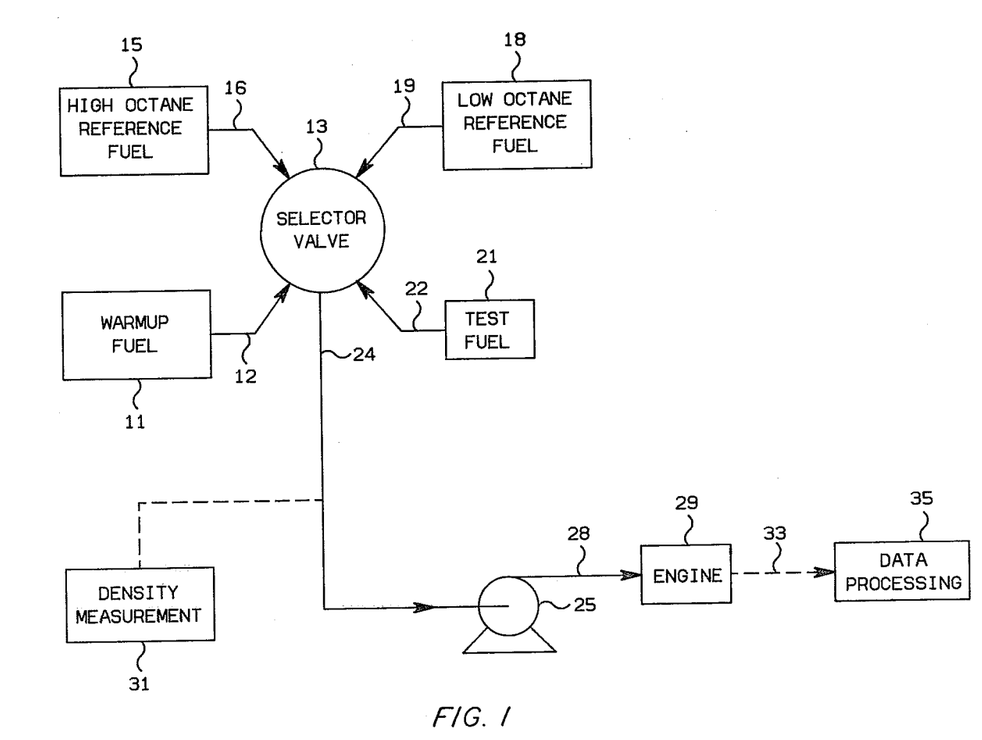
FIG. 1 is a simplified diagrammatic illustration of apparatus for determining the octane number of a fuel in accordance with the present invention.

Referring now to the drawings and in particular to FIG. 1, a warm-up fuel is provided from the supply 11 through conduit means 12 to the selector valve 13; a high octane reference fuel is provided from the supply 15 through conduit means 16 to the selector valve 13; a low octane reference fuel is provided from the supply 18 through conduit means 19 to the selector valve 13; and a test fuel is provided from the supply 21 through conduit means 22 to the selector valve 13. The supplies for the various fuels may be under pressure if desired or gravity flow may be utilized. A particular fuel is selected through use of the selector valve 13 and is provided through conduit means 24 to the pump 25. The fuel flowing through conduit means 24 is provided from the pump 25 through conduit means 28 to the engine 29. The pumping rate of the pump 25 is manipulated in such a manner that the fuel flowing through conduit means 28 flows at the mass flow rate which results in maximum knock.

It is noted that for a wide range of hydrocarbon base fuels such as aromatics, alkylates and catalytic cracker gasolines, the mass flow rate of the fuel which gives maximum knock is substantially constant for a particular engine operating at a particular speed. For example, the research octane number is determined in accordance with ASTM Method D-2699-79 by operating a standard ASTM-CFR engine at 600 RPM. Under these conditions the mass flow rate of each fuel which results in maximum knock is about 13 grams per minute. The required mass flow rate will vary with engine type and engine speed but once the mass flow rate that results in maximum knock for a particular engine operating at a particular speed is determined, this mass flow rate can be used for both the test fuel and the reference fuel.

Typically, the volume flow rate of whatever fuel is flowing through conduit means 28 will be known. Any suitable method may be utilized to determine the actual mass flow rate based on the known volume flow rate. Preferably, the density measurement of whatever fuel is flowing through conduit means 24 by the density measuring device 31 is utilized to determine the actual mass flow rate. A suitable density measuring device is a Metler-Parr Density measuring device manufactured by Metler. The density of the fuel is multiplied by the volume flow rate to give the actual mass flow rate. Other techniques such as weighing a known volume of the fuel and multiplying the weight of the known volume of fuel by the volume flow rate can be utilized. Whatever technique is used, the flow rate of the fuel flowing through conduit means 28 can be set directly to the mass flow rate which results in maximum knock by adjusting the volume flow rate until the desired mass flow rate is achieved. The successive approximation technique required by the ASTM methods is not required to find the flow rate of the fuel which will result in maximum knock.

A pressure transducer associated with the engine 29 monitors the cylinder pressure in the engine 29 and produces a voltage signal 33 which is proportional to the rate of change of the cylinder pressure. Signal 33 is processed by the data processing equipment 35 to derive the knock intensity for the particular fuel being provided to the engine 29. Since the octane number of the high octane reference fuel and low octane reference fuel are known, and it is known that the engine is operating at conditions which give maximum knock for each of the fuels which are provided to the engine 29, the octane number of the test fuel can be derived directly by comparing the knock intensity of the test fuel to the knock intensity of the high octane reference fuel and the low octane reference fuel. Signal 33 may be processed by the standard ASTM methods which utilize a detonation meter and a knock meter or may be processed by other data processing techniques which may involve a computer as will be described hereinafter in conjunction with the description of FIG. 3.

In operation, the warm-up fuel flowing from the supply 11 is utilized simply to warm up the engine 29 and may be utilized for any calibrations required. One of the reference fuels can be used for warm up purposes if desired. After the engine has been warmed up, the high octane reference fuel, low octane reference fuel and test fuel are then provided sequentially to the engine 29. The high octane reference fuel, low octane reference fuel and test fuel may be provided to the engine 29 in any order but preferably the high octane reference fuel is provided to the engine 29, then the low octane reference fuel and then the test fuel.

For most purposes, a four octane number spread between the reference fuels is desirable. The two most generally used sets of reference fuels are 90/94 and 96/100. The 90/94 pair of reference fuels is preferably used to rate test fuels in the range of about 88 to about 95 octane and the 96/100 pair of reference fuels is preferably used to rate test fuels in the range of about 95 to about 100 octane. Preferably, the high octane reference fuel and the low octane reference fuel should conform to the fuel requirements of ASTM Method D-2699-79 and D-2700-79 as outlined in sections 1, 3, 5, 6, and 8 and annexes 1–7 if the research octane number or motor octane number of a gasoline is being determined.

Any suitable apparatus for providing the different fuels sequentially to the pump 25 can be utilized. The use of the selector valve 13 is presently preferred but individual cutoff valves could be utilized with each of the fuel supplies being connected directly to the pump 25 if desired. A suitable selector valve 13 is a Whitey Selector valve, Model B-43ZF52.

Any suitable pump may be utilized to provide the fuel flow to the engine 29. A suitable fuel pump 25 is a FMI Lab Pump Model RP-P-SSY-0. Since the FMI pump provides volumetric flow rate, it is necessary to convert the volumetric flow rate to a mass flow rate. As has been previously stated, this is preferably done utilizing a density measurement of the various fuels flowing through the pump 25 but can be accomplished by utilizing any suitable apparatus which results in the fuels flowing to the engine 29 at the same substantially constant mass flow rate.

Any suitable engine may be utilized for the octane number determination. The engine 29 is preferably the ASTM-CFR engine which is required in the standard ASTM method for determining octane number. The ASTM-CFR engine is a one cylinder, four cycle engine which conforms to the requirements of ASTM Standard D-2699-79 and also includes a D-1 pressure transducer. Other engines may be required by other standard tests.

Figure 2:
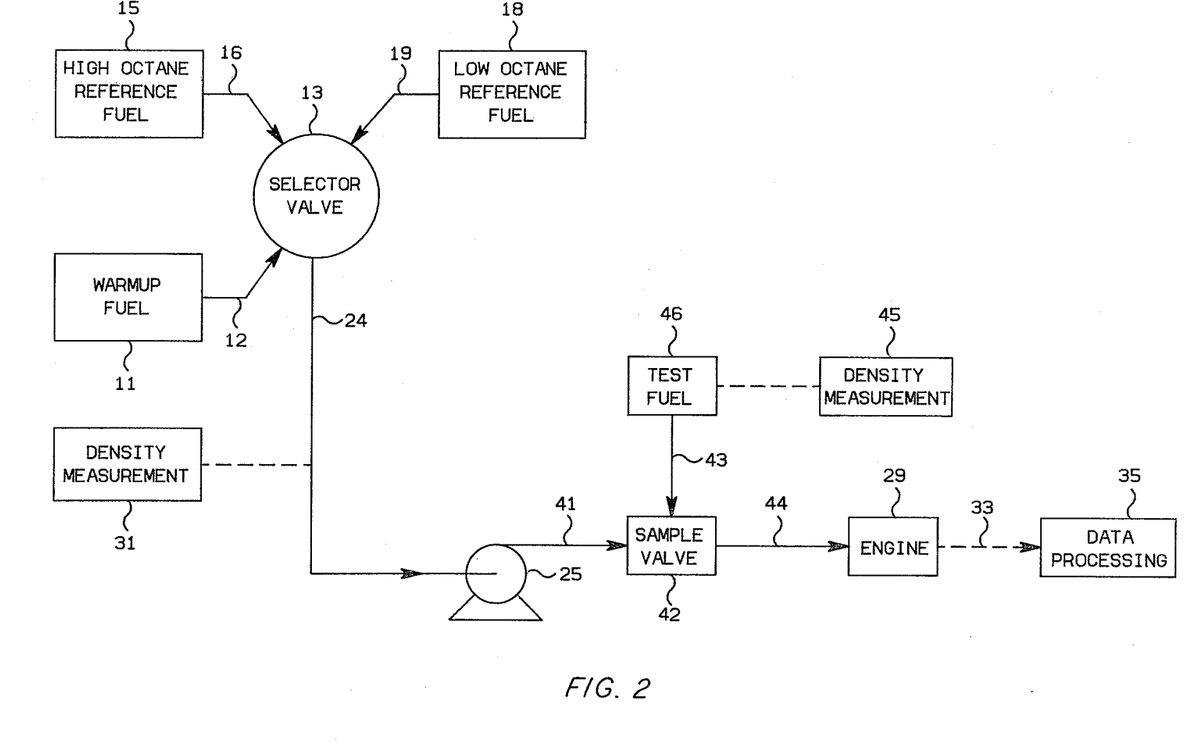
FIG. 2 is a simplified diagrammatic illustration of an embodiment of the invention which can be utilized where only a very small sample of the test fuel is available.

A variation of the present invention which results in the use of only a very small sample of the test fuel is illustrated in FIG. 2. Operation of the octane measuring system is essentially the same as that described in conjunction with FIG. 1 except for the use of the sample valve 42 which may be a model X valve manufactured by Applied Automation, Inc. Fuel flows from the pumping means 25 through conduit means 41 to the carrier fluid inlet of the sample valve 42 which is a well known device commonly utilized in chromatography. A test fuel is provided from the reservoir 46 through conduit means 43 to the sample inlet of the sample valve 42 to fill the sample loop of the sample valve 42. The fuel flowing through conduit means 41 is utilized as a carrier fluid. A measurement of the density of the test fuel in the reservoir 46 is provided by the density measuring device 45. In operation, the warm-up fuel, high octane reference fuel and low octane reference fuel are provided directly through the sample valve 42 to the engine 29 and the knock intensity for the high octane reference fuel and low octane reference fuel are determined as has been previously described. When it is desired to provide the test fuel to the engine 29, the pump 25 is first set to the flow rate which will provide maximum knock when the test fuel is flowing to the engine 29 based on the density measurement of the test fuel. The sample valve 42 is then switched such that the test fuel in the sample loop of the sample valve is provided to the engine 29 through conduit means 44. Again, the fuel flowing through conduit means 41 acts as a carrier fluid and essentially a slug of test fuel is injected into the engine 29 with the carrier fluid preceding and following the slug. The knock intensity when the test fuel is flowing to the engine 29 is determined and the octane number of the test fuel is derived as has been previously described.

Figure 3:
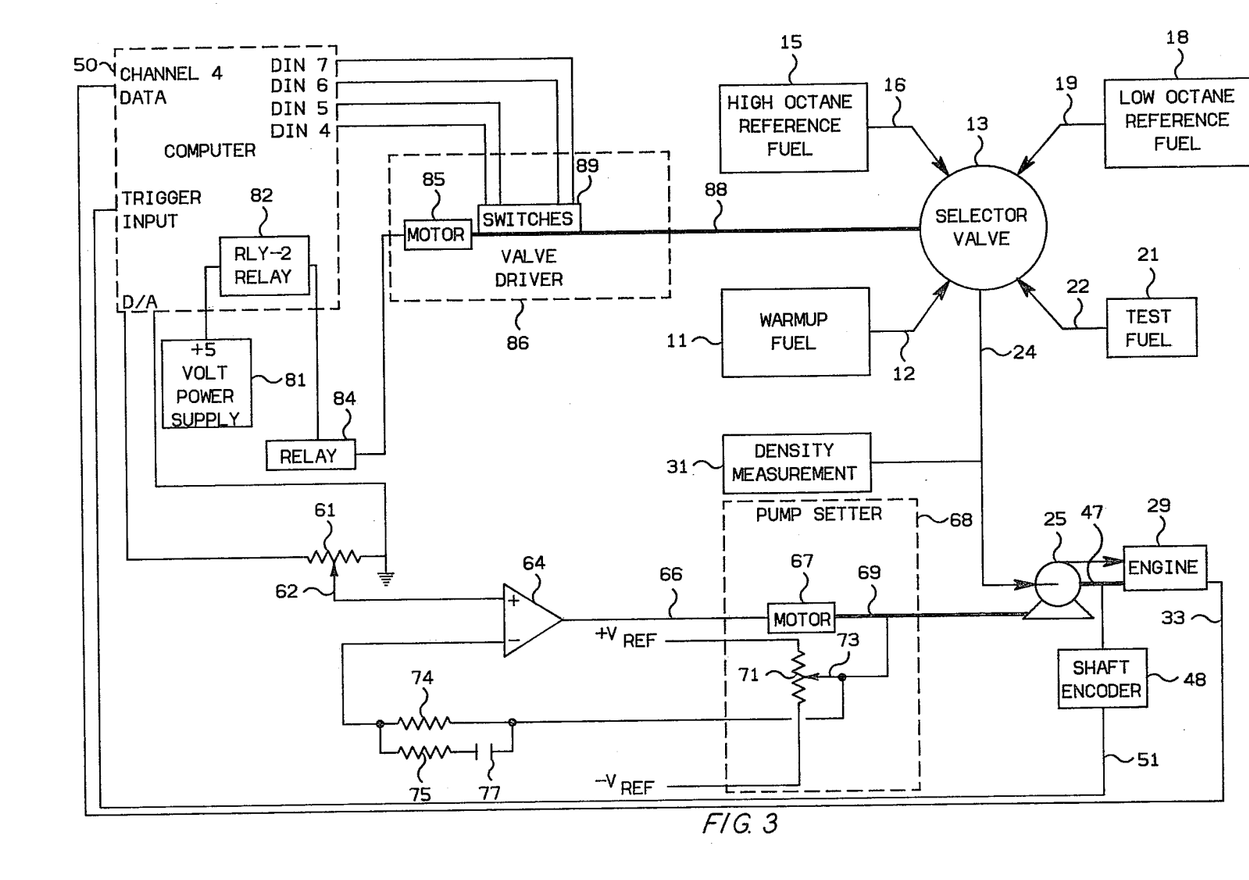
FIG. 3 is a diagrammatic illustration of the preferred computer controlled apparatus configuration for determining the octane number of a fuel in accordance with the present invention.

A preferred embodiment of the present invention in which the octane measuring system illustrated in FIG. 1 is under computer control is illustrated in FIG. 3. Referring now to FIG. 3, the octane measuring system is operated as in FIG. 1 except for the use of the computer to control the selector valve 13 and the pump 25. The engine 29 is preferably an ASTM-CFR engine as has been previously stated. The pump 25 is driven by a half-speed shaft 47 of the engine 29. A suitable shaft encoder 48 is a Disc Rotaswitch Shaft Encoder, Model X-701-360-T-C-L-TTL-SS manufactured by Disc Instruments. The shaft encoder 48 is operably connected to the half-speed shaft 47. The shaft encoder provides an output signal 51 which is a single transistor transistor logic (TTL) level pulse which is delivered once per engine cycle. Signal 51 is provided to the trigger input of the computer 50 and is utilized to provide timing information to the computer 50 which is preferably a Norland 3001 Processing Digital Oscilloscope manufactured by Norland Corporation.

Signal 33, which is representative of the rate of change of the engine cylinder pressure as has been previously described, is provided to the channel 4 data input of the computer 50. Signal 33 is utilized to derive the octane number of the test fuel as will be described more fully hereinafter.

The digital-to-analog converter outputs of the computer 50 are electrically connected to opposite poles of the potentiometer 61 (5KL). The wiper arm 62 of the potentiometer 61 is electrically connected to the non-inverting input of the operational amplifier 64 (Model 967 supplied by Analog Device Co.). The output signal 66 from the operational amplifier 64 is provided to the motor 67 which is associated with the pump setter 68 and is utilized to supply power to the motor 67. The drive shaft 69 of the motor 67 is utilized to set the pumping rate of the pump 25.

The potentiometer 71 is utilized to provide feedback information concerning the pumping rate of the pump 25. The wiper arm 73 of the potentiometer 71 moves in response to the position of the shaft 69 to indicate the pump flow rate. The wiper arm 73 is electrically connected through the parallel combination of resistors 74 (100KL) and 75 (10KL) and capacitor 77 (0.33 mf) to the inverting input of the operational amplifier 64.

A suitable pump setter 68 is a Motor Controlled Multi-turn Potentiometer No. 522-9505 distributed by Allied Electric. The manner in which the pump setter 68 and the circuitry associated with the pump setter 68 which interfaces the pump setter 68 to the computer 50 is utilized to manipulate the pumping rate of the pump 25 will be described more fully hereinafter.

A +5 volt power supply 81 supplies power to the RLY-2 relay 82 associated with the computer 50. When the relay 82 is closed, power is supplied from the +5 volt power supply 81 to the relay 84. When power is supplied from the +5 volt power supply 81, the relay 84 supplies power to the motor 85 which is associated with the valve driver 86. The shaft 88 associated with the motor 85 is utilized to manipulate the position of the selector valve 13.

A suitable valve driver 86 is a Hoke Operator part No. 0112,L2P manufactured by Hoke. The switches 89 associated with the valve driver 86 provide information regarding the position of the shaft 88 to the computer 50. The switches 89 are electrically connected to the DIN 4-DIN 7 inputs of the computer 50. The manner in which the valve driver 86 in conjunction with the computer 50 is utilized to control the position of the selector valve 13 will be described more fully hereinafter.

With the apparatus illustrated in FIG. 3 has been powered up and the computer programs set forth in Appendix I loaded into the computer 50, the digital-to-analog converter of the computer 50 establishes the pump flow rate required for the warm-up fuel to produce maximum knock from previously loaded density data. Preferably, the high octane reference fuel, low octane reference fuel and warm-up fuel are chosen to have the same density; thus, the same flow setting provides maximum knock for each of these fuels. Thus, it is necessary only to enter one density measurement for the warm-up fuel, high octane reference fuel and low octane reference fuel.

After the required flow rate has been entered into the computer 50, the engine 29 is then warmed up and the compression of the engine 29 is set based on the low octane reference fuel by the standard procedure set forth in ASTM 2699-79.

The output of the digital-to-analog converter of the computer 50 determines the voltage applied to the non-inverting input of the operational amplifier 64. The operational amplifier 64 compares the signal supplied by the Norland digital-to-analog converter through the potentiometer 61 to the voltage which is provided from the potentiometer 71 to the inverting input of the operational amplifier 64. The voltage applied to the inverting input of the operational amplifier 64 is proportional to the pumping rate of pump 25. The difference between the values of the signals applied to the inverting and non-inverting inputs of the operational amplifier 64 determines the magnitude of the signal which is provided from the output of the operational amplifier 64 to the motor 67. The pumping rate of the pump 25 is changed by the output of the operational amplifier 64 until the signals applied to the inverting and non-inverting inputs of the operational amplifier 64 are balanced. In this manner, the pumping rate of the pump 25 is controlled directly from the computer 50 by the digital-to-analog converter output of the computer 50.

After the engine 29 is warmed up, the computer 50 is supplied with the density of the test fuel, the octane number of the high octane reference fuel and the octane number of the low octane reference fuel if different from the warm-up fuel. The computer is then allowed to run the high octane reference fuel, low octane reference fuel and test fuel through the engine 29. Data is acquired and the octane number of the test fuel is determined.

When it is desired during the program sequence to switch the selector valve 13, the Norland computer 50 closes the relay 82 which supplies 5 volts to the relay 84. The relay 84 is turned on and power is supplied to the motor 85. The motor 85 rotates the selector valve 13 so that various fuel ports are connected singularly to the suction inlet of the pump 25. A cam on the drive shaft 88 energizes the switches 89 which are connected to the binary input lines of the Norland computer 50. When the switch position corresponding to the desired fuel is reached, the computer 50 opens the relay 82 to stop the motor 85.

The computer 50 automatically changes the position of the selector valve 13 as required to provide the different fuels to the engine 29. The pumping rate of the pump 25 is automatically set and adjusted to the pumping rate that provides a flow rate of fuel to the engine 29 resulting in a maximum knock condition for each particular fuel.

Data acquisition by the computer 50 consists of utilizing the shaft encoder 48 to trigger the computer 50. When the computer 50 is triggered, 1,024 data points 20 microseconds apart are acquired. This array of data is 20.48 milliseconds in length and centered about the combustion part of the engine cycle. This procedure is repeated 128 times and the results are averaged. After the data for the high octane reference fuel are acquired, similar data are acquired for the low octane reference fuel and the test fuel.

The thus acquired data is then processed to remove the low frequency normal combustion portion of the data and leave the higher frequency portion of the trace that is due to knocking combustion. The area of each of the traces that is due to knocking is then measured and stored in a register in the computer 50. The thus stored areas are directly related to the knock intensity and over a range of several octane numbers a plot of knock intensity versus octane number is a straight line. The reference fuel knock intensities are used to construct a calibration equation which is utilized to calculate the octane number of the test fuel.

Preferably, the data acquired by the computer 50 is Fourier transformed after averaging. This converts the data to the frequency domain and provides an easy means for filtering the low frequency terms. An inverse Fourier transform is then performed on the filtered data and the area of each trace is determined as has been previously described. Many other techniques could be utilized to process the data.

Figure 4:
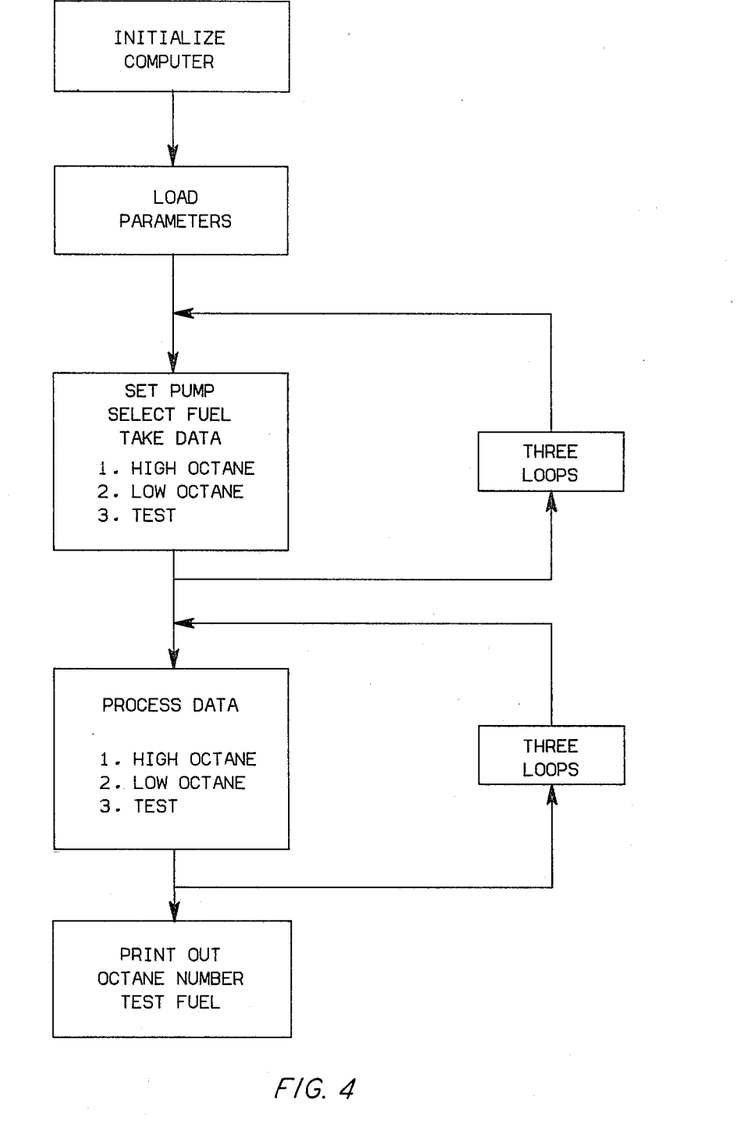
FIG. 4 is a flow chart illustrating the preferred method for determining the octane number of a fuel in accordance with the present invention.

A brief flow chart of the method of the present invention is illustrated in FIG. 4.

Many different types of software programs could be written in different languages and formats which would allow the Norland computer to carry out its required functions. While many different software programs could be developed to allow the Norland computer to accomplish its required functions, a suitable software program for the Norland computer is attached as Appendix I to the present application.

The invention has been described with particular reference to the standard ASTM methods for determining the octane number of gasoline. The ASTM methods require the use of the ASTM-CFR engine. It is again noted that the present invention is applicable to any octane measurement using any suitable engine. Once the mass flow rate which results in maximum knock is determined for one fuel for a particular engine operating at a particular RPM, all the fuels required for the octane measurement are provided to the engine at that same mass flow rate with maximum knock resulting for all the fuels. This results in savings in time and fuel as has been previously stated.

The invention has been described broadly and in terms of the presently preferred embodiment. Reasonable variations and modifications are possible by those skilled in the art within the scope of the described invention and the appended claims.

APPENDIX I

```
001    DPLY Q1 Q2 Q3 Q4 T/F
002      128.00  ==> SWEEP LIMIT
003       12.000 ==> INPUT BITS
004        2.0000E-05 ==> DECR
005        7.0000 ==> R5
006    DISK 99==> Q1
007        1.0000 ==> BIN B
008        0.0000 ==> I
009    INCI
010    R5 IF > I
011    STEP 2_.
012    END
013        1.0000 ==> BIN B
014    BIN H
015       16.000 IF > H/
016    STEP 3.
017    END
018    STEP 5_.
019        0.0000 ==> BIN B
020    PAUS
021    PAUS
022    DISK 06RUN
023    PAUS
024    PAUS
025    DISK 20RUN
026    PAUS
027    PAUS
028        0.0000 DISK 70A
029        0.0000 DISK 71A
030        0.0000 DISK 72A
```

```
031    0.0000 DISK 73A
032    0.0000 DISK 74A
033    0.0000 DISK 75A
034    0.0000 DISK 76A
035    0.0000 DISK 77A
036    0.0000 DISK 78A
037    0.0000 DISK 79A
038    0.0000 DISK 80A
039    0.0000 DISK 81A
040   DISK 70RUN
041   PAUS
042   PAUS
043   DPLY PROGRAM ==> DISK 01
001   DPLY Q1 Q2 Q3 Q4 T/F
002    12.000 ==> INPUT BITS
003    128.00 ==> SWEEP LIMIT
004    2.0000E-05 ==> DECR
005    7.0000 ==> R5
006    2.0000 ==> R6
007    1.0000 ==> R7
008    0.0000 ==> C
009    85.000 ==> R9
010    0.0000 ==> D
011   TRG.H
012    1.0000 ==> BIN B
013    0.0000 ==> I
014   INCI
015   R5 IF > I
016   STEP 2_.
017   END
018    1.0000 ==> BIN B
019   BIN H
020    16.000 IF > H
021   STEP 3:
022   END
023   STEP 5_.
024    0.0000 ==> BIN B
025   PAUS
026   PAUS
027   R0 ==> R3
028   R1 ==> R4
029   R4 - R3 ==> R4
030   DISK 07RUN
031   DPLY PROGRAM ==> DISK 06
```

```
001    1.0000E-03 IF > D
002    GOTO 6.
003    END
004    D * -1309.5 ==> E
005    E +  1622.9 ==> E
006    E ==> E
007    A' ==> DAC
008    1.0000 ==> BIN B
009    0.0000 ==> I
010    INCI
011    R5 IF > I
012    STEP 2_.
013    END
014    1.0000 ==> BIN B
015    BIN H
016    30.000 IF > H
017    STEP 3.
018    END
019    STEP 5_.
020    0.0000 ==> BIN B
021    C + 1.0000 ==> C
022    DPLY I DPLY
023    0.0000 ==> I
024    R9 IF > I
025    INCI
026    STEP 2_.
027    END
028    RESET
029    CONTINUE
030    Q4 ==> Q3
031    RESET
032    SINGLE CYCLE Q3
033    Q3 ==> Q2
034    1.0000 ==> BIN B
035    0.0000 ==> I
036    INCI
037    R5 IF > I
038    STEP 2_.
039    END
040    1.0000 ==> BIN B
041    BIN H
042    28.000 IF > H
043    STEP 3.
044    END
045    STEP 5_.
```

```
046     0.0000 ==> BIN B
047     0.0000 ==> I
048   R9 IF > I
049   INCI
050   STEP 2_.
051   END
052   RESET
053   CONTINUE
054   Q4 ==> Q3
055   E ==> DAC
056     1.0000 ==> BIN B
057     0.0000 ==> I
058   INCI
059   R5 IF > I
060   STEP 2_.
061   END
062     1.0000 ==> BIN B
063   BIN H
064    24.000 IF > H
065   STEP 3.
066   END
067   STEP 5_.
068     0.0000 ==> BIN B
069     0.0000 ==> I
070   R9 IF > I
071   INCI
072   STEP 2_.
073   END
074   DPLY DPLY
075   RESET
076   CONTINUE
077   Q1 ==> Q2
078     3.0000 ==> R8
079   A' ==> DAC
080     1.0000 ==> BIN B
081     0.0000 ==> I
082   INCI
083   R5 IF > I
084   STEP 2_.
085   END
086     1.0000 ==> BIN B
087   BIN H
088    16.000 IF > H
089   STEP 3.
090   END
```

```
091  STEP 5_.
092    0.0000 ==> BIN B
093  Q3 ==> Q4
094    9.0000 NPAVG Q4
095    3800.0 ==> HSETP
096  HSETP
097    .50000 ==> VLEVP
098  VLEVP'
099  PMAX'
100  COOR
101  H / DECR ==> R5
102    512.00 - R5 ==> R5
103  R5 SHIFT Q4
104  HANN Q4
105  FT Q4 ==> H2
106  H1 * H2 ==> H2
107  IFT H2 ==> H2
108    9.0000 NPAVG Q3
109    2800.0 ==> HSETP
110  HSETP
111    2800.0 ==> HSETQ
112  HSETQ
113  COOR
114  Q3 - V ==> Q3
115    4.0000E-02 ==> VLEVP
116    4.0000E-02 ==> VLEVQ
117  VLEVP'
118  VLEVQ'
119  COOR
120    5.0000E-03 IF > H
121  GOTO 168.
122  END
123  PMAX'
124  QMAX'
125    0.0000 ==> VLEVQ
126  VLEVQ'
127  QMIN'
128  PMIN
129  R8 IF > R6
130  STEP 6.
131  END
132  R8 IF > R7
133  STEP 11.
134  END
135  STEP 15.
```

```
136    AREA ==> C'
137    R8 -  1.0000 ==> R8
138    Q3 ==> Q2
139    RESET
140    SINGLE CYCLE Q2
141    Q1 ==> Q2
142    TRANSFER Q3
143    GOTO 93.
144    AREA ==> E'
145    R8 -  1.0000 ==> R8
146    RESET
147    SINGLE CYCLE Q3
148    TRANSFER Q4
149    GOTO 94.
150    AREA ==> B'
151    E' - C' ==> A
152    R4 / A ==> B
153    B * C' ==> R0
154    B * E' ==> R1
155    B * B' ==> R2
156    R3 - R0 ==> A
157    R0 + A ==> R0
158    R1 + A ==> R1
159    R2 + A ==> R2
160    PRINT C D E R0 R1 R2 C' E' B' PRINT

161    Q3 ==> Q4
162    TRANSFER Q3
163    TRANSFER Q2
164    PAUS
165    PAUS
166     7.0000 ==> R5
167    GOTO 1.
168    PRINT C H PRINT
169    GOTO 164.
170    DPLY PROGRAM ==> DISK 07
```

That which is claimed is:

1. Apparatus for determining the octane number of a test fuel comprising:

an engine means having a fuel inlet;

a pumping means having a suction inlet and a discharge outlet;

means for providing fuel from the discharge outlet of said pumping means to the fuel inlet of said engine means;

means for providing a first reference fuel to the suction inlet of said pumping means;

means for providing a second reference fuel to the suction inlet of said pumping means;

means for providing a test fuel to the suction inlet of said pumping means;

means for manipulating the flow of said first reference fuel, said second reference fuel and said test fuel to the suction inlet of said pumping means in such a manner that only one fuel is provided to the suction inlet of said pumping means at any one time;

means for manipulating the pumping rate of said pumping means in such a manner that said first reference fuel, said second reference fuel and said test fuel are each provided to the fuel inlet of said engine means at the same substantially constant mass flow rate which results in substantially maximum knocking conditions when each of said first reference fuel, said second reference fuel, and said test fuel are flowing to said engine means; and means for establishing a first signal representative of the rate of change of the cylinder pressure in said engine means when said first reference fuel is flowing to the fuel inlet of said engine means, for establishing a second signal representative of the rate of change of the cylinder pressure in said engine means when said second reference fuel is flowing to the fuel inlet of said engine means, and for establishing a third signal representative of the rate of change of the cylinder pressure of said engine means when said test fuel is flowing to the fuel inlet of said engine means.

2. Apparatus in accordance with claim 1 wherein said means for providing said first reference fuel to the suction inlet of said pumping means, said means for providing said second reference fuel to the suction inlet of said pumping means, said means for providing said test fuel to the suction inlet of said pumping means, and said means for manipulating the flow of said first reference fuel, said second reference fuel and said test fuel to the suction inlet of said pumping means comprises:

a selector valve means having at least first, second and third input ports and at least one output port in fluid communication with the suction inlet of said pumping means;

a fuel reservoir for said first reference fuel having a fluid outlet in fluid communication with a first fluid inlet of said selector valve means;

a fuel reservoir for said second reference fuel having a fluid outlet in fluid communication with a second fluid inlet of said selector valve means;

a fuel reservoir for said test fuel having a fluid outlet in fluid communication with a third fluid inlet of said selector valve means; and means for manipulating said selector valve means so as to provide said first reference fuel, said second reference fuel and said test fuel sequentially to the suction inlet of said pumping means.

3. Apparatus in accordance with claim 1 wherein said means for manipulating the pumping rate of said pumping means comprises:

means for determining the density of said first reference fuel, said second reference fuel and said test fuel; and means for manipulating the pumping rate of said pumping means in response to the density of said first reference fuel when said first reference fuel is flowing through said pumping means, in response to the density of said second reference fuel when said second reference fuel is flowing through said pumping means or in response to the density of said test fuel when said test fuel is flowing through said pumping means.

4. Apparatus in accordance with claim 1 wherein said means for establishing said first signal, said second signal and said third signal comprises a pressure transducer.

5. Apparatus for determining the octane number of a test fuel comprising:

an engine means having a fuel inlet;

a pumping means having a suction inlet and a discharge outlet;

a sample valve means having a carrier fluid inlet, a sample fluid inlet, a fluid outlet and a sample loop;

means for providing fuel from the discharge outlet of said pumping means to the carrier fluid inlet of said sample valve means;

means for providing fuel from the fluid outlet of said sample valve means to the fuel inlet of said engine means;

means for providing a first reference fuel to the suction inlet of said pumping means;

means for providing a second reference fuel to the suction inlet of said pumping means;

means for manipulating the flow of said first reference fuel and said second reference fuel to the suction inlet of said pumping means in such a manner that only one fuel is provided to the suction inlet of said pumping means at any one time;

means for providing a test fuel to the sample fluid inlet of said sample valve means to thereby fill the sample loop of said sample valve means with said test fuel; and means for manipulating the pumping rate of said pumping means in such a manner that said first reference fuel and said second reference fuel are each provided to the fuel inlet of said engine means at the same substantially constant mass flow rate which results in substantially maximum knocking conditions when each of said first reference fuel and said second reference fuel are flowing to said engine means, wherein said sample valve means is actuated so as to provide the test fuel in said sample loop of said sample valve means to the fluid outlet of said sample valve means when it is desired to provide said test fuel to said engine means at the same substantially constant mass flow rate used for said first reference fuel and said second reference fuel; and means for establishing a first signal representative of the rate of change of the cylinder pressure in said engine means when said first reference fuel is flowing to the fuel inlet of said engine means, for establishing a second signal representative of the rate of change of the cylinder pressure in said engine means when said second reference fuel is flowing to the fuel inlet of said engine means, and for establishing a third signal representative of the rate of change of the cylinder pressure of said engine means when said test fuel is flowing to the fuel inlet of said engine means.

6. Apparatus in accordance with claim 5 wherein said means for providing said first reference fuel to the suction inlet of said pumping means, said means for providing said second reference fuel to the suction inlet of said pumping means, and said means for manipulating the flow of said first reference fuel and said second reference fuel to the suction inlet of said pumping means comprises:

a selector valve means having at least first and second input ports and at least one output port in fluid communication with the suction inlet of said pumping means;

a fuel reservoir for said first reference fuel having a fluid outlet in fluid communication with a first fluid inlet of said selector valve means;

a fuel reservoir for said second reference fuel having a fluid outlet in fluid communication with a second fluid inlet of said selector valve means; and means for manipulating said selector valve means so as to provide said first reference fuel and said second reference fuel sequentially to the suction inlet of said pumping means.

7. Apparatus in accordance with claim 5 wherein said means for manipulating the pumping rate of said pumping means comprises:

means for determining the density of said first reference fuel, said second reference fuel and said test fuel; and means for manipulating the pumping rate of said pumping means in response to the density of said first reference fuel when said first reference fuel is flowing to the fuel inlet of said engine means, in response to the density of said second reference fuel when said second reference fuel is flowing to the fuel inlet of said engine means or in response to the density of said test fuel when said test fuel is flowing to the fuel inlet of said engine means.

8. A method for determining the octane number of a test fuel comprising the steps of:

providing a first reference fuel having a first known octane number to the fuel inlet of an engine at a first mass flow rate which will result in substantially maximum knocking conditions;

establishing a first signal representative of the rate of change of the cylinder pressure in said engine when said first reference fuel is flowing to the fuel inlet of said engine;

providing a second reference fuel having a second known octane number to the fuel inlet of said engine at said first mass flow rate, wherein said second known octane number is different from said first known octane number;

establishing a second signal representative of the rate of change of the cylinder pressure in said engine when said second reference fuel is flowing to the fuel inlet of said engine;

providing a test fuel having an unknown octane number to the fuel inlet of said engine at said first mass flow rate;

establishing a third signal representative of the rate of change of the cylinder pressure in said engine when said test fuel is flowing to the fuel inlet of said engine; and establishing the octane number of said test fuel in response to said first, second and third signals, wherein said steps of providing said first reference fuel, said second reference fuel and said test fuel to the fuel inlet of said engine at said first mass flow rate comprise:

determining the density of said first reference fuel, said second reference fuel and said test fuel;

multiplying the volume flow rate of the particular fuel flowing to the fuel inlet of said engine by the density of that particular fuel to determine the actual mass flow rate of the particular fuel flowing to the fuel inlet of said engine; and manipulating the volume flow rate of the particular fuel flowing to the fuel inlet of said engine until said first mass flow rate is achieved.

9. A method in accordance with claim 8 wherein said first reference fuel has an octane number of 94, said second reference fuel has an octane number of 90 and said test fuel has an octane number in the range of about 88 to about 95.

10. A method in accordance with claim 8 wherein said first reference fuel has an octane number of 100, said second reference fuel has an octane number of 96 and said test fuel has an octane number in the range of about 95 to about 100.

11. A method in accordance with claim 8 wherein said step of establishing the octane number of said test fuel in response to said first, second and third signals comprises:

acquiring a plurality of first arrays of data centered about the combustion part of the cycle of said engine when said first reference fuel is flowing to the fuel inlet of said engine;

averaging said first arrays of data;

filtering the low frequency normal combustion portion of the averaged first arrays of data;

determining a first knock intensity based on the filtered, averaged first array of data;

acquiring a plurality of second arrays of data when said second reference fuel is flowing to the fuel inlet of said engine;

averaging said second arrays of data;

filtering the low frequency normal combustion portion of the average second arrays of data;

deriving a second knock intensity based on the filtered, averaged second arrays of data;

acquiring a plurality of third arrays of data when said test fuel is flowing to the fuel inlet of said engine;

averaging said plurality of third arrays of data;

filtering the low frequency normal combustion portion of the averaged third arrays of data;

deriving a third knock intensity based on the filtered, averaged third arrays of data; and calculating the octane number of said test fuel based on a comparison of said first, second and third knock intensities.

12. A method for determining the octane number of a test fuel comprising the steps of:

providing a first reference fuel having a first known octane number to the fuel inlet of an engine at a first mass flow rate which will result in substantially maximum knocking conditions;

establishing a first signal representative of the rate of change of the cylinder pressure in said engine when said first reference fuel is flowing to the fuel inlet of said engine;

providing a second reference fuel having a second known octane number to the fuel inlet of said engine at said first mass flow rate, wherein said second known octane number is different from said first known octane number;

establishing a second signal representative of the rate of change of the cylinder pressure in said engine when said second reference fuel is flowing to the fuel inlet of said engine;

providing a test fuel having an unknown octane number to the fuel inlet of said engine at said first mass flow rate;

establishing a third signal representative of the rate of change of the cylinder pressure in said engine when said test fuel is flowing to the fuel inlet of said engine;

establishing the octane number of said test fuel in response to said first, second and third signals, wherein said steps of providing said first reference fuel, said second reference fuel and said test fuel to the fuel inlet of said engine at said first mass flow rate comprise:

determining the density of said first reference fuel, said second reference fuel and said test fuel;

multiplying the volume flow rate of said first reference fuel, when said first reference fuel is flowing to the fuel inlet of said engine, by the density of said first reference fuel to determine the mass flow rate of said first reference fuel;

manipulating the volume flow rate of said first reference fuel, when said reference fuel is flowing to the fuel inlet of said engine, until said first mass flow rate is achieved;

multiplying the volume flow rate of said second reference fuel, when said second reference fuel is flowing to the fuel inlet of said engine, by the density of said second reference fuel to determine the mass flow rate of said first reference fuel;

manipulating the volume flow rate of said second reference fuel, when said second reference fuel is flowing to the fuel inlet of said engine, until said first mass flow rate is achieved;

multiplying the volume flow rate of the reference fuel flowing to the fuel inlet of said engine by the density of said test fuel to determine what the mass flow rate would be if said test fuel were flowing to the fuel inlet of said engine at the volume flow rate of the reference fuel flowing to the fuel inlet of said engine;

manipulating the volume flow rate of the reference fuel flowing to the fuel inlet of said engine until said first mass flow rate would be achieved if said test fuel were flowing to said engine at that same volume flow rate; and injecting a slug of said test fuel into the reference fuel flowing to the fuel inlet of said engine to thereby provide said test fuel to the fuel inlet of said engine at said first mass flow rate.

* * * * *